United States Patent [19]
Schultz

[11] Patent Number: 5,717,054
[45] Date of Patent: Feb. 10, 1998

[54] EPOXY RESINS CONSISTING OF FLEXIBLE CHAINS TERMINATED WITH GLYCIDYLOXYPHENYL GROUPS FOR USE IN MICROELECTRONICS ADHESIVES

[75] Inventor: Rose Ann Schultz, Princeton, N.J.

[73] Assignee: National Starch & Chemical Investment Holding Corp., Wilmington, Del.

[21] Appl. No.: 656,619

[22] Filed: May 31, 1996

Related U.S. Application Data

[63] Continuation-in-part of Ser. No. 482,541, Jun. 7, 1995, abandoned.

[51] Int. Cl.[6] .................. C07D 303/12; C07D 303/16; C08G 59/20; C08G 59/24
[52] U.S. Cl. .................. 528/100; 549/552; 549/560
[58] Field of Search .................. 560/201; 564/155; 549/552, 560, 549; 528/100

[56] References Cited

U.S. PATENT DOCUMENTS

| | | | |
|---|---|---|---|
| 3,522,210 | 7/1970 | Sellers et al. | 260/47 |
| 4,110,354 | 8/1978 | Bertram et al. | 260/348.14 |
| 4,367,328 | 1/1983 | Bertram et al. | 549/522 |
| 5,536,855 | 7/1996 | Schultz et al. | 549/539 |

FOREIGN PATENT DOCUMENTS

| | | | |
|---|---|---|---|
| 0 028 024 A1 | 5/1981 | European Pat. Off. | C07D 303/16 |
| 0 028 024 | 6/1981 | European Pat. Off. | C07D 303/16 |
| 0 205 402 | 12/1986 | European Pat. Off. | C07D 303/24 |
| 0 205 402 A2 | 12/1986 | European Pat. Off. | C07D 303/24 |
| 0 272 442 A2 | 6/1988 | European Pat. Off. | C08G 59/32 |
| 0 397 317 | 11/1990 | European Pat. Off. | C07D 303/24 |
| 0 397 317 A1 | 11/1990 | European Pat. Off. | C07D 303/24 |
| 0 459 591 | 4/1991 | European Pat. Off. | C08G 59/38 |
| 0 459 591 A2 | 12/1991 | European Pat. Off. | C08G 59/38 |
| 0 747 370 A1 | 12/1996 | European Pat. Off. | C07D 303/28 |
| 0 747 371 A1 | 12/1996 | European Pat. Off. | C07D 303/46 |
| 1017612 | 1/1963 | United Kingdom . | |
| WO 95/23794 | 9/1995 | WIPO | C07D 303/16 |

OTHER PUBLICATIONS

JP45–005781 Abstract, Chem Abstracts, 72:133868 (1970).

*Primary Examiner*—Donald R. Wilson
*Attorney, Agent, or Firm*—Jane E. Gennaro

[57] ABSTRACT

This invention relates to flexible epoxy resins that have a structural composition comprising an oligomeric backbone of alkylene or alkyleneoxy repeat units, terminated with an aromatic moiety bearing one or more epoxy functionalities.

9 Claims, 4 Drawing Sheets

EPOXY RESINS CONSISTING OF FLEXIBLE CHAINS TERMINATED WITH GLYCIDYLOXYPHENYL GROUPS FOR USE IN MICROELECTRONICS ADHESIVES

This application is a continuation-in-part of Ser. No. 08/482,541, filed 07 Jun. 1995, to be abandoned.

FIELD OF THE INVENTION

This invention is directed to flexible epoxy compounds for use in microelectronics adhesives that can be rapidly cured and that have low or no ionic contamination, and to processes for their syntheses.

BACKGROUND OF THE INVENTION

One step in the manufacture of semiconductor integrated circuits is the bonding of a silicon chip or die with an adhesive to a copper frame from which extend metal conductor leads. The bonded die and lead frame assembly is encapsulated within a polymeric sealant and connected to external circuitry by way of the metal conductor leads that extend through the encapsulation.

Epoxy compounds are preferred as the die attach or encapsulating adhesive due to their superior adhesive strength. The epoxies conventionally used are the aromatic epoxies, due to their strength, but these are inherently rigid and brittle. During the manufacturing process the adhesives and substrates are subjected to repeated thermal cycling. If the adhesives and substrates have widely disparate coefficients of thermal expansion, the stress of thermal cycling can lead to adhesive failure, substrate warpage, or fracture of the die. Thus, a crucial requirement for an adhesive destined for microelectronics use is that it be strong and flexible to absorb the stress of thermal cycling.

A second crucial criterion is that the adhesives be capable of rapidly curing to meet the speeds of assembly line processing. The fast cure times required, typically 30–60 seconds at about 175°–200° C., are known as snap-cure. This combination of criteria, adhesive strength, flexibility, and ability to be snap-cured, is difficult to attain in one adhesive.

It is also crucial that the epoxy formulations be free of ionic contamination, particularly sodium and chloride ions, and free of bonded chlorine. These contaminants can cause corrosion of the metal leads in semiconductor devices and the ultimate failure of the devices.

To add flexibility, epoxies can be co-reacted with an aliphatic flexibilizer; this, however, reduces adhesive strength because the level of aromatic moieties is lowered. The addition of a flexibilizer also reduces the ability of the adhesive to be snap-cured because the flexibilizer has a high molecular weight per epoxy. Moreover, when the aliphatic and aromatic epoxies are cured, they may not co-react due to a difference in reactivity rates; low molecular weight compounds may volatilize out before cure, and high molecular weight compounds may not completely cure. This combination of factors, sometimes even a problem for slow cure formulations, is fatal for achieving snap-cure.

As a possible solution to some of these problems, it is known to combine aromatic moieties with aliphatic moieties in the backbone of the same polymer, but the currently available polymers of this type have a high ratio of aromatic to aliphatic moieties, which results in a loss of flexibility. Additionally, the method of preparation of these materials results in high chlorine contamination, which is deleterious in microelectronics applications. The polymers also have high viscosities, which requires the addition of a solvent as a diluent. During snap-cure, the curing is sometimes faster than complete solvent volatilization, which leads to voids in the cured adhesive, and potential failure of the microelectronics chip or device. Thus, low viscosity materials, which eliminate the need for solvent, are preferred.

It is also imperative in the construction of electronic devices to have minimal weight loss (no outgassing) of the adhesive that bonds the die to the lead frame. This is important both during cure of the die to the lead frame, and post cure during wire-bonding processes (~200° C.) or when the circuit is encapsulated or molded. Weight loss during cure or post cure should be minimized so that any volatiles escaping from the adhesive do not redeposit on the die surface. Any redeposit can lead to die top delamination during or after the molding operation. Further, outgassing after the molding operation, but during solder reflow can result in a pressure build-up that can lead to package cracks.

The problems associated with providing strength to flexible compounds, and with snap-cure and thermal stability (low weight loss at elevated temperature), are amplified as the microelectronics industry moves toward larger and larger die sizes. This creates a continuing need for improved flexible epoxies, which have strength, and that can be formulated into snap-cured die attach adhesives.

SUMMARY OF THE INVENTION

Figure 1:
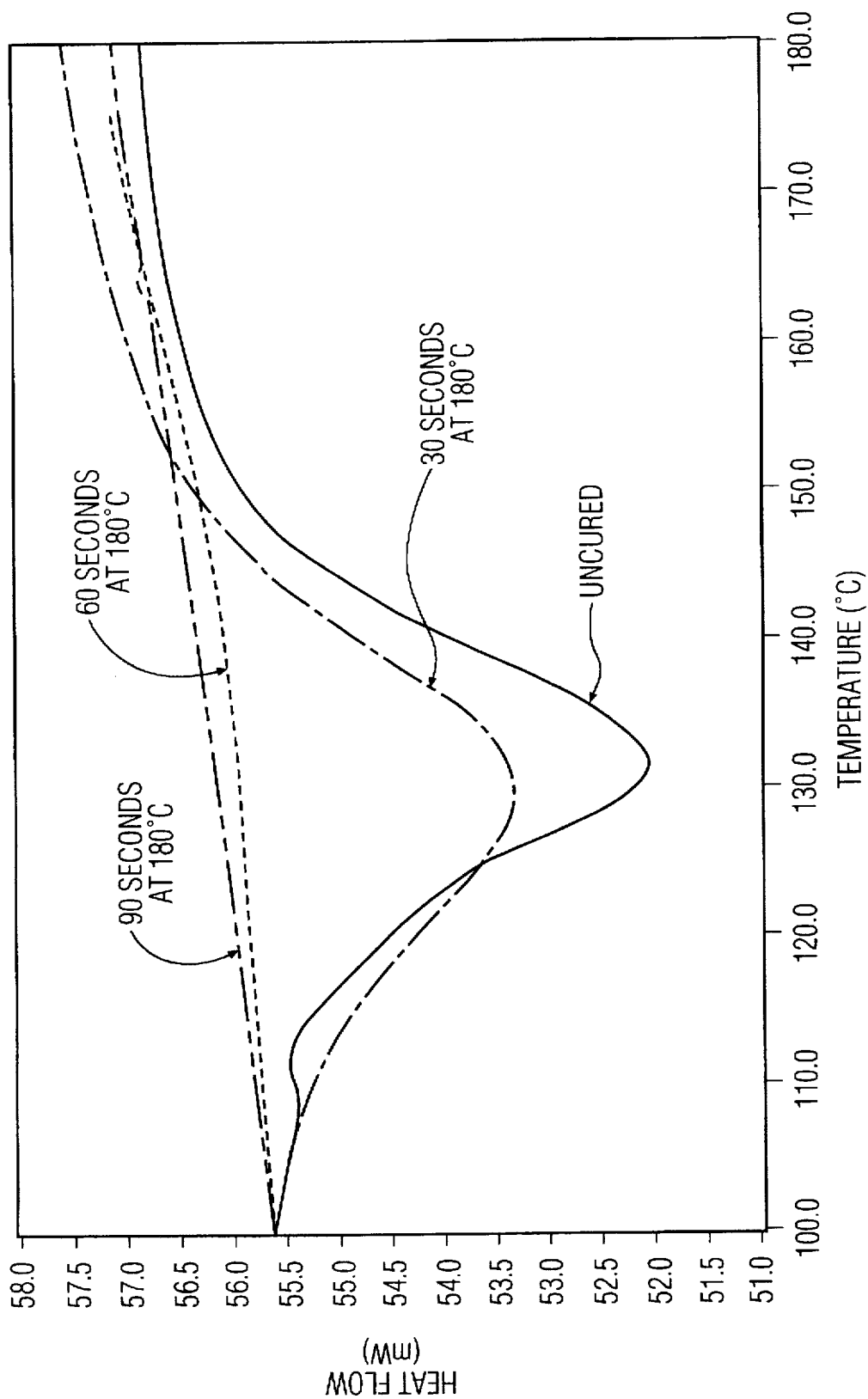
FIG. 1 is a DSC graph of inventive epoxy D showing the change in exotherm as the epoxy is cured. There is a linear relationship between the area over the curve and percent cure. Similar DSC curves for other of the inventive epoxies were used to generate the data plotted in FIG. 2.
Figure 2:
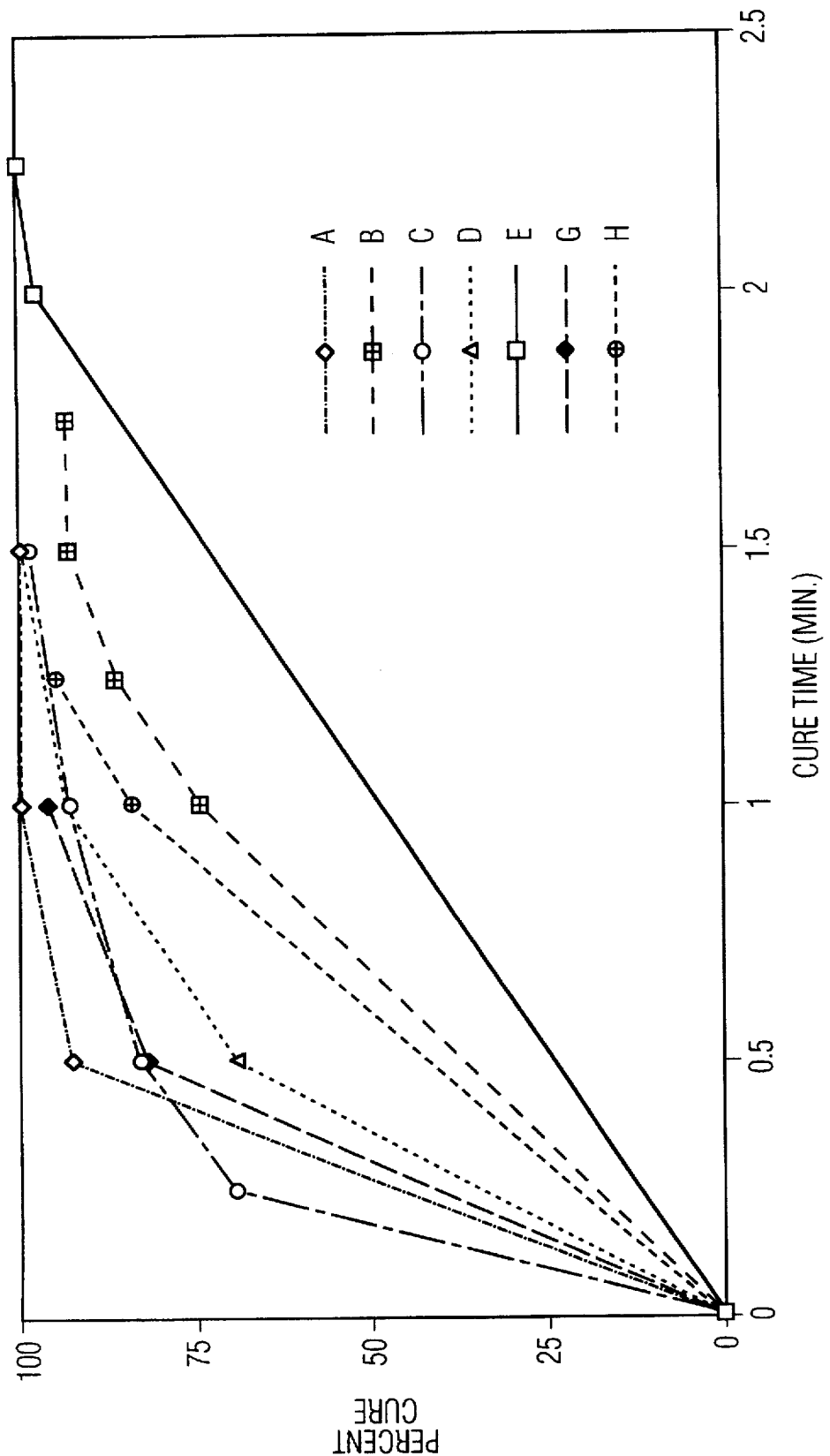
FIG. 2 is a graph of the percent cure of inventive sample epoxy resins versus cure time.

This invention relates to flexible epoxy resins that can be used to formulate snap-curable die attach adhesives, encapsulants, and coatings. The epoxies are prepared by a synthetic route that uses epichlorohydrin early in the synthesis at a point when contaminants can be easily removed, resulting in low levels of ionic contaminants, less than about 0.1% by weight, compared to prior art compositions, which contain impurities at higher levels. This is a significant difference for industrial applications. Moreover, the synthetic routes permit the preparation of discrete chemical structures, rather than mixes of various resins.

The epoxy resins are liquids or solids at room temperature, and can have Tg values when cured of less than or equal to 100° C.

In another embodiment, this invention pertains to adhesives made with these epoxies, for use in microelectronics applications. The flexibility of these compounds is retained when the epoxies are formulated with conductive material, such as silver flakes, and used to bond silicon chips to a metal lead frame substrate. The cured epoxies demonstrate a high radius of curvature, greater than or equal to 300 mm. (The higher the radius of curvature, the less chip warpage, which in turn implies a flexible adhesive.)

The cured epoxies also demonstrate good adhesive strength, measured as die shear strength. Die shear is a measure of the force required to remove a bonded chip from the metal substrate, which for these compounds is greater than or equal to 10 MPa when cured under snap-cure conditions. The epoxies can be formulated into adhesives that snap-cure and exhibit no loss of flexibility or strength. Preferably the formulation will comprise 20–100 parts by weight of the flexible epoxy and 80–0 parts of an aromatic O-glycidyl ether (to a total of 100 parts), a curing agent, a conductive filler, and optionally 20–50 parts of a phenolic hardener per hundred parts of epoxy resin (pphr).

DETAILED DESCRIPTION OF THE INVENTION

The structural composition of the epoxy resins comprises an oligomeric backbone of alkylene or alkyleneoxy repeat units, of moderate length to provide flexibility, but still maintain sufficient crosslink density to yield useful adhesive properties. The flexible backbone is terminated on one or both ends with an aromatic moiety bearing one or more epoxy functionalities. Thus, the compounds have no more than two aromatic moieties, which exist only at the termini. Restricting the number and the location of aromatic moieties in the polymer backbone maintains the strength imparted to the cured material by the aromatic moieties and maximizes the flexibility imparted to the cured material by the aliphatic moieties. A discussion of the synthetic routes to these compounds, and a discussion of previously known routes, will further elucidate the structures of the compounds of this invention.

Routes to flexible epoxy resins are known, and include the use of the glycidyl ester of dimerized fatty acid and glycidyl-terminated polyurethanes (or glycidyl carbamates). These materials are inferior for microelectronics application as it has been found that the oxiranylmethoxy moiety attached directly to a carbonyl group (as it is for both of the above) catastrophically lose weight at elevated temperature (temperatures near 200° C.) when cured under the snap-cure conditions required for current electronic device manufacture. This is a major disadvantage since snap-curing is conducted near 200° C. and the die/lead frame assembly is subjected to temperatures of 200°–250° C. during the wire bonding process and after molding during the solder reflow operation. Another problem in the manufacture of electronic devices is that severe outgassing (release of volatiles) must be minimized throughout the entire device manufacture process. The compounds of this invention have snap-cure property and greatly improved thermal stability to temperatures of 300° C.

Other routes to flexible epoxy resins are known in which the resins are prepared from epichlorohydrin and a diphenol compound bearing a flexible backbone. These compounds possess high chlorine contamination (usually >0.2%). It is imperative for microelectronic application to minimize all sources of corrosive ions (including organic bound chlorine).

To accomplish the required features of snap cure, low stress, low volatility, and high purity the following sequence has been followed in this invention. The epoxy functionality is built onto an aromatic ring by an epichlorohydrin reaction. Effecting this transformation on a small molecule allows for easy purification by post-treating with caustic as is known in the art, and by distillation or (re)crystallization. The aromatic ring may have more than one epoxy group and also contains another functionality that allows it to be attached to the ends of a flexible chain. This functionality can be a carboxylic acid (so is derived from a benzoic acid) or a hydroxymethyl (so is derived from a benzyl alcohol). The aromatic ring can optionally bear other non-interfering groups.

The attachment to the flexible chain can be carried out as with the benzoic acid derivatives by a dehydrative process (using a carbodiimide/hydroxybenzotriazole system) where the flexible chain bears amine groups at the termini. Thus, a benzamide functionality is generated during this coupling process. The attachment to the flexible chain can be carried out as with the benzyl alcohol derivatives in one of two ways. The first is again a dehydrative process (using a carbodiimide/dimethylaminopyridine system) in which the flexible chain bears carboxylic groups at the termini. Thus, a benzyl ester functionality is generated during this coupling process. The second method involves condensing the benzyl alcohol derivative with a flexible chain bearing isocyanate groups at the termini. Thus, an O-benzyl carbamate functionality is generated during this coupling process.

It is known to condense glycidyl ether benzyl alcohols with isocyanates, but the known methods generate a mixture of materials by co-reacting diisocyanates with mono- and di-alcohol functionalized phenyl glycidyl ethers. This results in a mixture of components with epoxy functionality at the termini as well as along the urethane backbone. In contrast, the compounds of this invention bear the epoxy functionality only at the termini, and the only urethane groups are present at the termini by virtue of the condensation and not in the backbone of the polymer. The flexible chains comprise only alkylene or alkyleneoxy units.

Further, the literature disclosing these known compounds only describe room temperature cure with an aliphatic diamine. It could not be anticipated that the compounds of this invention would function as snap-cure epoxy resins with high thermal stability in the presence of an imidazole catalyst, especially with respect to our finding of poor thermal stability with the O-glycidyl carbamate as shown in a comparative example.

A brief description of the preferred synthetic routes follows.

Synthetic Routes

The preferred synthetic route comprises attaching an alkylene or alkyleneoxy chain to an aromatic compound, which is an aromatic nucleus substituted with one or more glycidyl ether groups and with a functional group that will react with a functional group on the alkylene or alkyleneoxy chain. Typically, the aromatic compound is a benzene ring substituted with a glycidyl ether group and the functional group, which preferably is acid or hydroxy.

The aromatic ring may also be substituted with a $C_{1-8}$ alkyl, $C_{1-5}$ alkoxy or aryl or alkylaryl, $C_{1-5}$ perfluoroalkyl, or $C_{1-5}$ acyl. As used here, alkyl refers to a hydrocarbon group derived from an alkane and has the generic formula $C_nH_{2n+1}$, alkoxy refers to an alkyl group also containing oxygen; aryl refers to a group having the ring structure characteristic of benzene; alkylaryl refers to a group containing both alkyl and aryl structures; perfluoroalkyl refers to an alkyl group in which all of the hydrogens are substituted with fluorine; and acyl refers to an organic acid group in which the OH of the carboxyl group is replaced by some other substituent, in this case, the phenyl ring to which it is attached.

The alkylene or alkyleneoxy chain may have 10–50 carbon atoms, but is typically prepared from dimer acid, a 36 carbon chain, which is the product resulting from the dimerization process of unsaturated fatty acids, or the chain may be prepared from the corresponding dimer diamine or dimer diisocyanate, all of which are commercially available.

Amine-terminated alkylene or alkyleneoxy chains may be reacted with a benzoic acid, substituted with an epoxy group in a dehydrative coupling process. The reaction takes place in the presence of a dehydration system, which provides an amide linkage between the alkylene or alkyleneoxy chain and the substituted benzoic acid derivative. Such dehydration systems are known in the art. A preferred system uses carbodiimides, for example, dicyclohexyl carbodiimide (as used later herein, DCC) with a hydroxy-benzotriazole catalyst in a suitable solvent.

Preferred substituted benzoic acids include glycidyl-substituted benzoic acids, or glycidyloxy-substituted benzoic acids. A preferred compound is 3-glycidyloxy benzoic acid.

Alternatively, the alkylene or alkyleneoxy chains may be terminated in a carboxylic acid and reacted with a glycidyl- or glycidyloxy-substituted benzyl alcohol using a dehydrative carbodiimide and pyridine catalyst coupling reaction.

Another method comprises the condensation of an isocyanate terminated alkylene or alkyleneoxy chain with a benzyl alcohol substituted with either a glycidyl or glycidyl ether group.

Preferred compounds made from these synthetic routes are represented by the following structural formulas in which C-34 and C-36 are the residual hydrocarbon chains of the respective dimer acid, dimer diamine, or dimer diisocyanate (as described above) reacted according to the above described synthetic routes.

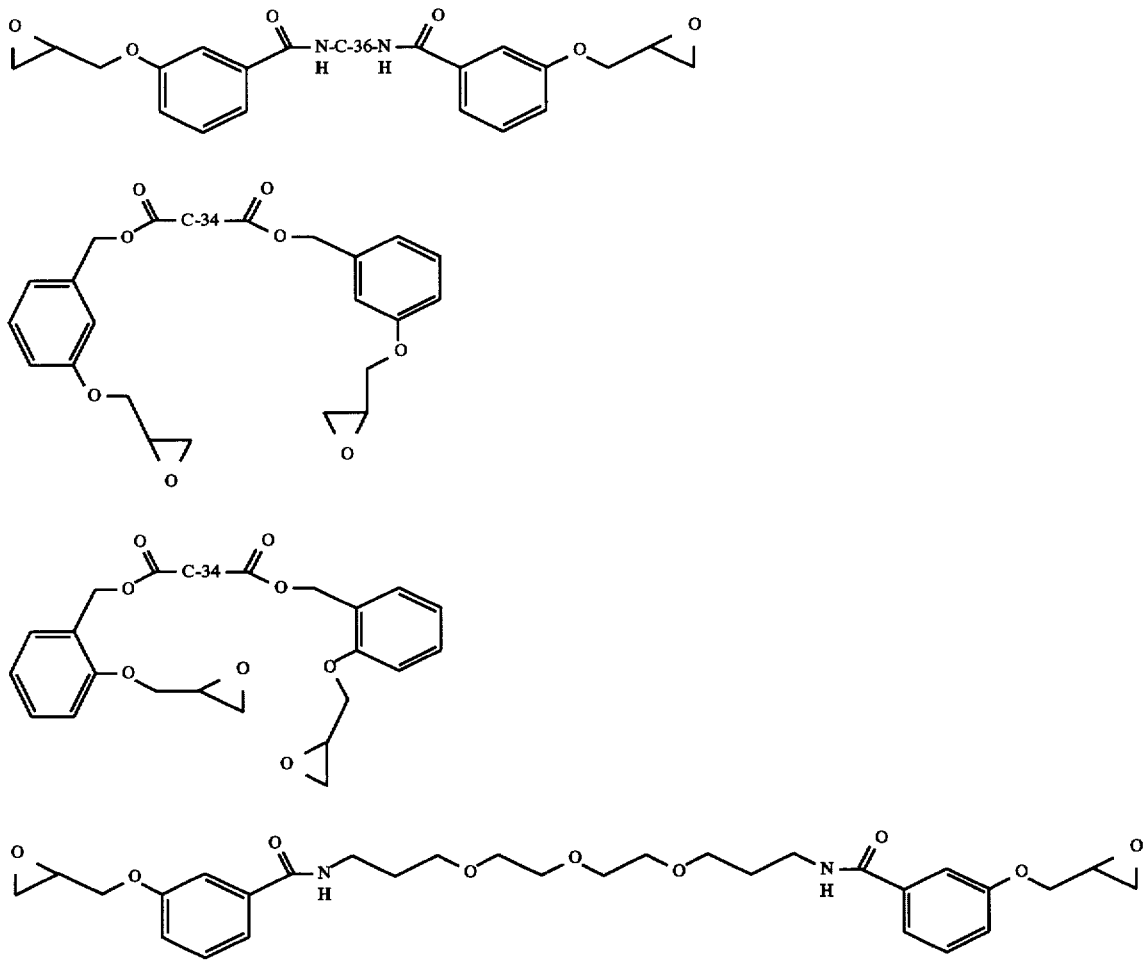

-continued
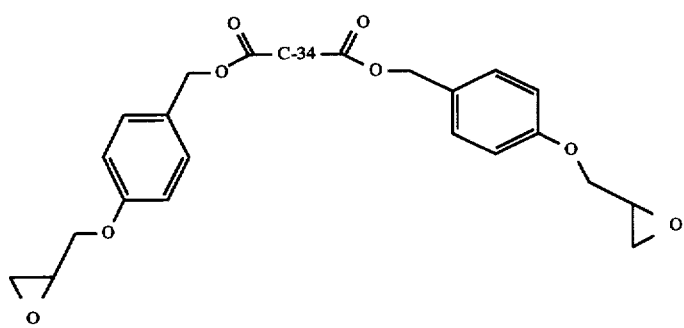
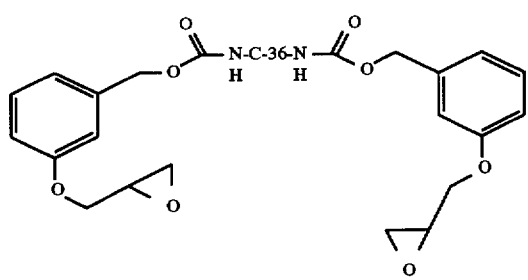
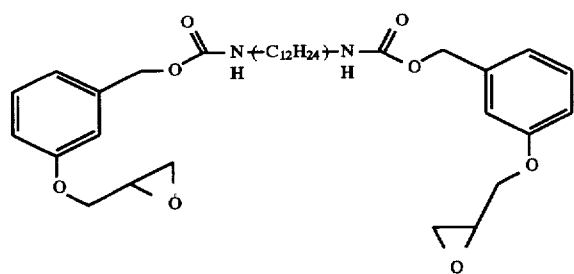
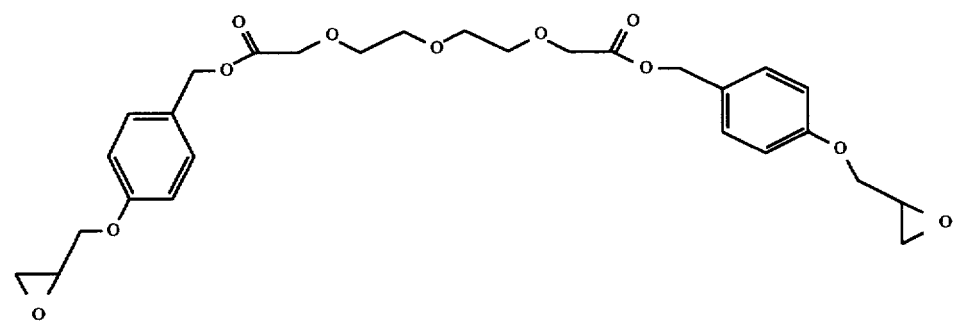
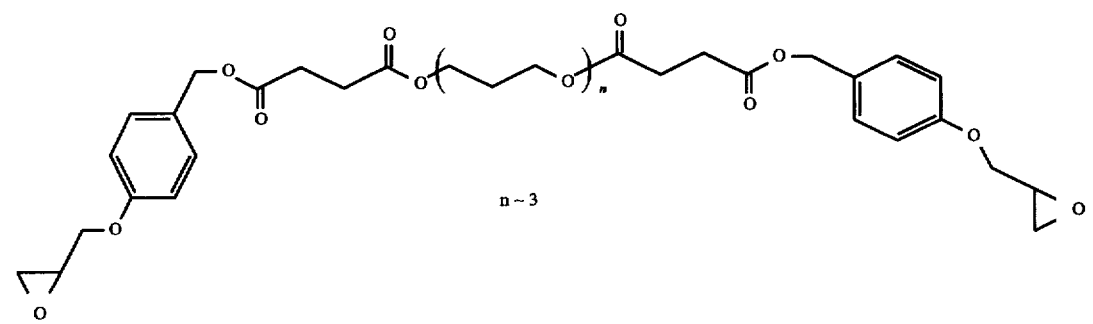

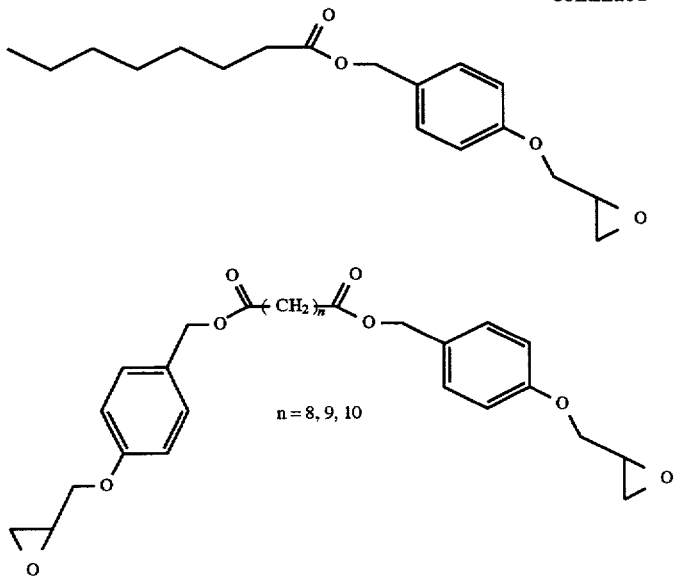

Formulation of Snap-Cure Adhesives

The flexible epoxy compositions of this invention exhibit good adhesive strength and flexibility, and can be formulated into adhesives that have the ability to be snap-cured. The preferred snap-cure formulations will contain 20–100 parts by weight of the flexible epoxy and 80–0 parts by weight of an aromatic O-glycidyl ether resin (to total 100 parts), a curing catalyst, and optionally a phenolic hardener or one or more fillers. In general the curing catalyst is an imidazole catalyst, present in an amount of about 5–10 parts per hundred parts resin, and the filler is thermally or electrically conductive, such as silver flakes, although other electrically or thermally conductive fillers, as well as silica, may be used. The filler is preferably present in an amount of about 25% by volume of the adhesive formulation.

The aromatic O-glycidyl ether (aromatic epoxy) will be substituted with one or more aromatic rings, and optionally with one or more $C_1$–$C_3$ alkyl groups. The aromatic epoxies will have an epoxy equivalent weight (WPE, weight per epoxy) of 200 or less, and will be derived form the corresponding phenolic hardeners. Exemplary aromatic epoxies are bisphenol-F diglycidyl ether, bisphenol-A diglycidyl ether, resorcinol diglycidyl ether, and the epoxy phenol novolaks.

The adhesive formulation may further contain 20–50 parts per hundred parts of resin of a phenolic hardener having one or more hydroxyl groups per aromatic ring (from which are derived the aromatic epoxide described above). Exemplary phenolic hardeners are the commercially available phenol novolak resins, bisphenol-F, bisphenol-A and resorcinol. The addition of the phenolic resin serves to improve the adhesion strength of the formulation after exposure to moisture and thermal shock at 250° C., and to prevent bleeding of the flexible epoxy out of the formulation.

In general any effective curing catalyst in an effective catalytic amount can be used. The preferred curing catalyst is an imidazole catalyst, and typically is present in an amount of about 5 parts per hundred parts resin. Preferable imidazole catalysts are imidazole, 2-ethylimidazole, 2-ethyl-4-methylimidazole, 2-phenylimididazole, 2-phenyl-4-methylimidazole, and 2-undecylimidazole.

The filler may be any of the thermally or electrically conductive materials, or silica, known to be suitable for microelectronics applications, used in any effective amount. For many applications, the preferred filler is silver flakes, although other electrically or thermally conductive fillers may be used, and is preferably present in an amount of about 25% by volume of the adhesive formulation.

EXAMPLES

The following examples illustrate the preparation of representative epoxy resins. The evaluation test methods are given and the performance results tabulated.

The examples also disclose snap-curable die attach adhesive formulations that contain the flexible epoxies and the O-glycidyl ether aromatic epoxies.

Test Methods

The amount of hydrolyzable chlorine was determined by the following method: Weigh accurately 1–5 g (to the nearest 0.1 mg) of resin into a clean, 125 ml Erlenmeyer flask with a Teflon® coated magnetic stir bar. Add 40 ml of 0.1N KOH dissolved in methanol. Place flask fitted with reflux condenser into a water bath heated by magnetic stirrer/hot plate unit. Reflux the stirred solution for exactly 15 minutes, then remove the flask, and allow it to cool to room temperature. Transfer the liquid into a clean 250 ml beaker. Rinse the sample flask three times with 50 ml portions of methanol, transferring the liquid into the beaker. Add 10 ml of glacial acetic acid and titrate the chloride ion potentiometrically to the end point with 0.005N $AgNO_3$ solution. Calculate the hydrolyzable chloride content in ppm as follows:

$$\text{Chloride (ppm)} = \frac{\text{(ml titrant) (N AgNO}_3\text{) (3.55} \times 10^4\text{)}}{\text{weight sample g}}$$

The amount of total chlorine was determined by the following method: Accurately weigh 1–5 g (to the nearest 0.1 mg) of resin into a clean Erlenmeyer flask with a magnetic stir bar. Add 30 ml of dioxane and 15 ml of 3N KOH solution in ethanol. Place flask fitted with a reflux condensor into a 100 ° C. water bath heated on a stirrer/hot plate unit. Allow sample solution to reflux for 30 minutes. Remove flask and allow it to cool to room temperature.

Transfer the liquid into a clean 400 ml beaker. Rinse the sample flask three times with 50 ml portions of methanol, transferring the liquid into the beaker. Add 100 ml of glacial acetic acid. Titrate potentiometrically with 0.005N AgNO₃ solution to the end point using a silver electrode with a KNO₃ salt bridge. Calculate the chloride content in ppm as described above.

Example I

In this example, 3-glycidyloxybenzoic acid (aromatic nucleus substituted with a glycidyl group and an acid group) is reacted with an alkylene chain terminated with amine groups to form α,ω-bis(3-glycidyloxybenzamide. The alkylene is a 36 carbon diamine, sold under the trademark Versamine 552 by Henkel.

The preparation of 3-glycidyloxybenzoic acid was conducted by first epoxidizing the ethyl ester of 3-hydroxybenzoate with epichlorohydrin, and then hydrolyzing the ester functionality to the acid. The use of the epichlorohydrin at this early stage in the synthesis and on this low molecular weight molecule makes purification and removal of the ionic and bound chlorine contaminants relatively easy.

Preparation of α,ω-bis(3-glycidyloxybenzamide of Versamine 552 diamine (EPOXY A)

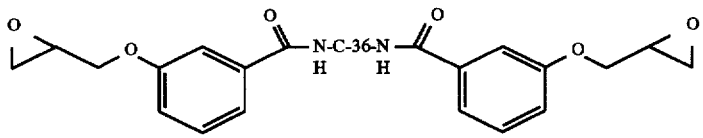

Preparation of the ethyl ester epoxide: Into a 3 liter flask, fitted with mechanical stirrer, nitrogen purge and condenser, were charged ethyl 3-hydroxybenzoate (200 g, 1.2048 mol), epichlorohydrin (334.6 g), potassium carbonate (261.16 g; ~321 mesh powder, pro-dried at 120% in vacuum oven for several hours), and methyl ethyl ketone (1 L). This mixture was heated with a heating mantle to gentle reflux (~85° C.) overnight. Analysis by GC (10 m glass capillary, 100° to 250° C. at 10°/min) indicated incomplete reaction. A further 10 mL epichlorohydrin was added and reflux continued for 3 hours at which point the reaction was judged complete by gas chromatography (GC) trace. The contents were cooled and the salts removed by suction filtration. The solvent was removed on a roto-vap to 35° C. The residue was taken up in methyl isobutyl ketone and washed with 5% NaOH (2×400 mL). The organic phase was dried over MgSO₄. The solvent was removed on the roto-vap to 60° C. The yellow oil was distilled on a Kugelrohr apparatus at 100° C./0.1 mmHg to provide a clear colorless oil (176.56 g, 66% yield). H-NMR and IR spectra were consistent with expected structure.

Hydrolysis of the ethyl ester: Into a one liter single neck flask immersed in a cool water bath with magnetic stir bar was charged ethyl 3-glycidyloxybenzoate (60 g), 0.66N KOH (400 mL), and dioxane (450 mL). This mixture was allowed to stir for 1.5 hours at which point it was judged complete by the virtual disappearance of starting material in the reversed phase TLC (Whatman MKC₁₈F reverse phase plates, eluent 25 mL tetrahydrofuran/25mL H₂O with 10 drops conc. H₃PO₄). The mixture was reduced to minimum volume on a roto-vap at 30° C. for 30 min. The residue was washed with ethyl ether (to remove any unhydrolyzed material). The aqueous layer was then acidified with 50% H₂SO₄ to a pH ~2. Ammonium sulfate was added to nearly saturate the aqueous layer at which point he product began to oil out. The product was extracted into ethyl acetate (EtOAc) (2×~500 mL). The solvent was removed on a roto-vap and then the Kugelrohr was used to remove trace solvent and water. The ¹H-NMR was consistent with the desired product structure.

Preparation of α,ω-bis(3-glycidyloxybenzamide) of Versamine 552: To a one L 3-neck flask fitted with mechanical stirrer, 250 mL slow-add funnel, condenser, and N₂ purge was charged Versamine 552 (47.22 g). To this was added 250 mL CH₂Cl₂, followed by 3-glycidyloxybenzoic acid (35.04 g) and HOBt (1-hydroxybenzotriazole, 2.4388 g) with additional CH₂Cl₂ rinsing. This mixture was stirred for 15 minutes, and then a solution of 40.80 g dicyclohexyl carbodiimide (DCC) in 200 mL CH₂Cl₂ was added in a dropwise fashion to the reaction flask. Within 15 minutes of the start of the DCC addition, the precipitation of by-product dicyclohexyl urea (DCU) was observed. The reaction progress was monitored by IR spectroscopy and no observable change was detected between 4 and 5 hours of reaction time. The excess DCC was then quenched by the addition of 50% aqueous acetic acid (5 mL) and stirring was continued until the DCC absorbance in the IR trace had disappeared (~1.5 hr). The solution was cooled and the DCU was removed by suction filtration then the solvent was removed on a roto-vap to 30° C. The residue was taken up in EtOAc and was washed with 5% NaHCO₃ (3×400 mL) and the organic layer was refrigerated overnight. The product solution was washed again with 5% NaHCO₃ (1×400 mL), then 2% triethylamine (1×200 mL), and finally water (1×400 mL). The organic layer was treated with MgSO₄, filtered, and then stirred over Amberlyst 15 ion exchange resin (H⁺ form, ~100 mL) for 1.5 hr. The resin was removed by filtration, and the product dried over MgSO₄, filtered and solvent removed on the roto-vap. Residual solvent was further removed by a Kugelrohr apparatus (80° C./0.25 mmHg/20 min.). The viscous amber oil (74.1 g, 91% yield) was characterized by IR, ¹H and ¹³C -NMR and found to be consistent with the expected structure. The epoxy content was measured as WPE=481 (theoretical WPE=443).

Example II

Preparation of α,ω-bis(3-glycidyloxybenzamide of 4,7,10-trioxa-1,13-tridecane diamine (EPOXY F)

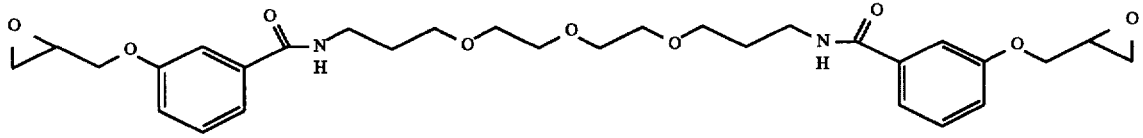

The preparation of this compound was conducted similarly to that in Example I. The 3-glycidyloxybenzoic acid was prepared as described in Example I. To a 250 mL multi-neck flask equipped with magnetic stir bar, thermometer, slow addition funnel and $N_2$ purge was charged the 3-glycidyloxybenzoic acid (19.8 g, 0.101 mole) in 50 mL methylene chloride. To this was added the diamine (11.01 g, 0.05 mole) and 25 mL methylene chloride. A slight exotherm was observed. The reaction mixture was chilled in an ice bath to 0°–5° C., when 1-hydroxybenzotriazole (1.35 g, 0.01 mole) was added followed by the addition of a solution of 1,3-dicyclohexylcarbodiimide DCC (22.9 g, 0.1111 mole) in 25 mL methylene chloride over 5 minutes. The addition funnel was rinsed with another 25 mL methylene chloride. The reaction temperature was held at 5°–20° C. After 15 minutes evidence of dicyclohexyl urea by-product was observed. The reaction was monitored by IR and after three hours of reaction time the mixture was filtered and the solvent removed under vacuum on a rotary evaporator to 30° C. The product was dissolved in 200 mL ethyl acetate and to this was added a solution of 12 mL $H_2O$/3 mL acetic acid in three portions over 2 hours with mixing to effect quenching of excess DCC which was determined by IR (2112 $cm^{-1}$). The organic layer was then washed with saturated $NaHCO_3$ (4×100 mL), and saturated $Na_2SO_4$ (1×100 mL). The organic layer was dried over $MgSO_4$ and filtered over Celite. The solvent was removed under vacuum on a rotary evaporator to 80° C. Complete solvent removal was accomplished by placing the material on a Kugelrohr apparatus to 90° C./0.25 mmHg. The product was isolated as a viscous yellow oil (25.65 g, 90% yield). The epoxy content was measured as WPE=314 (theoretical WPE=286). The product was characterized by IR and $^1$H-NMR spectroscopy.

Example III

In this example, glycidyloxybenzyl alcohols were reacted with dimer acid, sold under the trademark Empol 1024 by Henkel to form the bis(glycidyloxybenzyl) esters of dimer acid.

Preparation of bis(3-glycidyloxybenzyl) ester of dimer acid (EPOXY B-1)

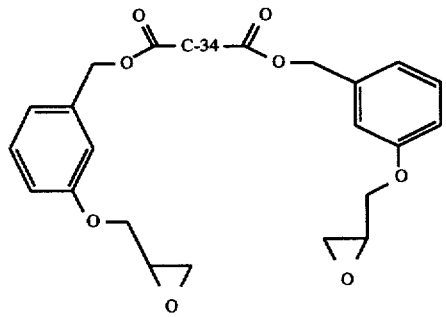

Preparation of 3-glycidyloxybenzyl alcohol: The epoxidation procedure was conducted similarly to that described in Example I.

To a two L multi-neck flask fitted with mechanical stirrer, condenser, and thermometer was charged epichlorohydrin (277 mL, 3.542 mol) and 250 mL methyl ethyl ketone. The 3-hydroxybenzyl alcohol (200 g, 1.61 mol) was added as a solid rinsing with 500 mL methyl ethyl ketone (MEK). Then the potassium carbonate (320 g, 2.31 mol, pre-dried to 120° C. in vac. oven/3 hr.) was added as a powder. The mixture was heated with an oil bath to a mild reflux (~80° C.). After six hours at reflux the reaction was determined to be complete by the absence of starting benzyl alcohol in the GC trace (5 m glass capillary, 150° to 200° C. at 10°/min). The mixture was cooled to room temperature and filtered rinsing with MEK. The solvent was removed on the roto-vap, and the residue was redissolved in methyl isobutyl ketone (350 mL). The organic layer was washed with 5% NaOH (1×200 mL) and a severe emulsion resulted. The system was allowed to settle and the bulk of the aqueous layer was removed. The organic layer was then washed with 10% $Na_2SO_4$ (5×200 mL) until the pH was ~7. The organic layer was dried over $MgSO_4$, filtered and the solvent removed on the roto-vap to 80° C. The product was collected as a distillate on the Kugelrohr apparatus at 120° to 140° C./2.0 mmHg (earlier attempt distillation at 110° C./0.1 mmHg). The clear almost colorless oil (190.6 g, 66% yield) was characterized by IR, $^1$H, and $^{13}$C-NMR and was found to corroborate assigned structure. The epoxy content was measured as WPE=180 (theoretical WPE=180).

Preparation of the bis(3-glycidyloxybenzyl) ester of dimer acid (EPOXY B-1): To a one L multi-neck flask with mechanical stirrer, thermometer, slow add funnel, and $N_2$ purge was charged 3-glycidyloxybenzyl alcohol (91.62 g, 0.509 mol), and Empol 1024 dimer acid (143.71 g). To this was added 250 mL $CH_2Cl_2$ and DMAP (dimethylaminopyridine; 0.61 g, 1 mol percent based on COOH), and the mixture immediately cooled in an ice bath to maintain temperature at 4° to 10° C. throughout the reaction. DCC solution (DCC: 104.85 g, 0.509 mol in 60 mL $CH_2Cl_2$) was added dropwise through a slow addition funnel over a one hour period. At four hours after the completion of the slow add the ester absorbance was maximized and the DCC absorbance was minimized in the IR trace. The reaction mixture was then filtered and rinsed with $CH_2Cl_2$. The filtrate was stirred over 30 mL Amberlyst 15 ion exchange resin ($H^+$ form) for 30 minutes and filtered. To this filtrate was added 50% aqueous acetic acid (5 mL) and this was stirred until the DCC disappeared in the IR trace (30 min). To this was added solid $NaHCO_3$ with stirring until the pH was ~7. This was filtered to remove salts and the filtrate was stored in the freezer overnight. The organic layer was dried with $MgSO_4$ and filtered rinsing with $CH_2Cl_2$. The solvent was removed first on a roto-vap, then on a Kugelrohr apparatus to 110° C./0.25 mmHg. The final product was a brown oil (217.8, 96% yield), and was characterized by IR, $^1$H, and $^{13}$C-NMR spectroscopy which corroborated the assigned structure. The epoxy content was measured as WPE=448 (theoretical WPE=453).

Preparation of bis(2-glycidyloxybenzyl) ester of dimer acid (EPOXY B-2)

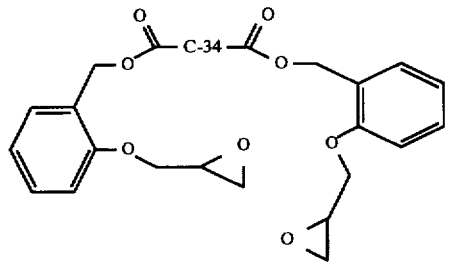

Preparation of 2-glycidyloxybenzyl alcohol: This compound was prepared as described above except that the starting phenol was 2-hydroxybenzyl alcohol. The product was isolated and purified by distillation (36% yield). Characterization was accomplished by IR and $^1$H-NMR spectroscopy. The epoxy content was measured as WPE=180.

Preparation of the bis(2-glycidyloxybenzyl) ester of dimer acid: This material was prepared exactly as described above except that 2-glycidyloxybenzyl alcohol was used. The product was isolated in 90% yield and was characterized by IR and $^1$H-NMR spectroscopy. The epoxy equivalent weight was measured as WPE=456 (theoretical WPE=450).

Preparation of bis(4-glycidyloxybenzyl) ester of dimer acid (EPOXY B-3)

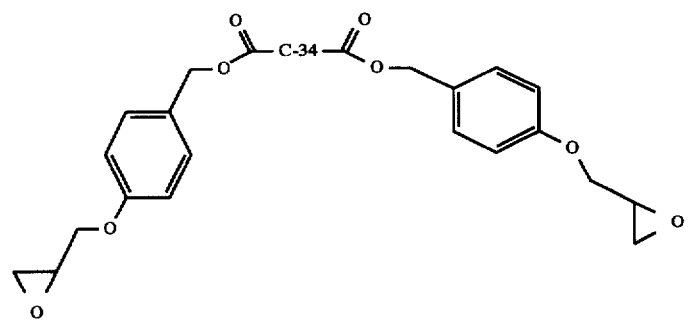

Preparation of 4-glycidyloxybenzyl alcohol: This compound was prepared as described above except that the starting phenol was 4-hydroxybenzyl alcohol. The product was isolated and purified by distillation at which point the material formed a white crystalline solid (45% yield). Characterization was accomplished by IR and $^1$H-NMR spectroscopy. The epoxy content was measured as WPE=179.

Preparation of the bis(4-glycidyloxybenzyl) ester of dimer acid: This material was prepared exactly as described above except that 4-glycidyloxybenzyl alcohol was used. The product was isolated in 91% yield and was characterized by IR and $^1$H-NMR spectroscopy. The epoxy equivalent weight was measured as WPE=445 (theoretical WPE=450).

Example IV

In this example, the diisocyanate from dimer acid (sold under the tradename DDI-1410 by Henkel) and 1,12-diisocyanatododecane were reacted with 3-glycidyloxxbenzyl alcohol to form the corresponding carbamates.

Preparation of bis-O-(3-glycidyloxybenzyl) carbamate of dimer diisocyanate (EPOXY D)

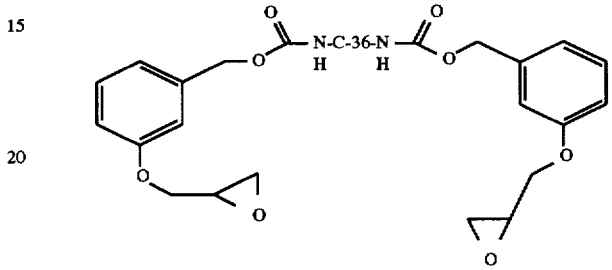

Dimer diisocyanate (DD1-1410, 146.52 g, 0.4898 mol NCO) was weighed directly into a 500 mL multi-neck flask equipped with mechanical stirrer, thermometer, and $N_2$ purge. Then, 3-glycidyoxlbenzyl alcohol (90 g, 0.4996 mol) was added along with 150 mL toluene. To this non-homogeneous mixture was added one drop of dibutyl tin dilaurate (DBTDL) from a plastic disposable pipette. The mixture became completely clear and homogeneous 20 minutes after the addition of the DBTDL. A mild exotherm to 28° C. was observed while the flask was immersed in a cool water bath. The temperature was not allowed to pass 30° C. After 7 hours of reaction time (disappearance of NCO in the IR trace), the reaction mixture was passed over a silica column prepared in a one L slow add funnel by first slurrying ~250 mL of 30–60 mesh silica in EtOAc then layering on top of this ~150 mL of 70–230 mesh silica. The product was eluted with ~1.5 L EtOAc. The solvent was removed on a roto-vap, then on a Kugelrohr apparatus to 128° C./0.1 mmHg. The product was a pale yellow viscous oil (231.5 g, 98.6% yield) that solidified upon storage in a freezer and that was structurally confirmed by IR, 1H, and $^{13}$C-NMR spectroscopy. The epoxy content was measured as WPE=475 (theoretical WPE=479).

Preparation of bis-O-(3-glycidyloxybenzyl) carbamate of 1,12-diisocyanatododecane (EPOXY K)

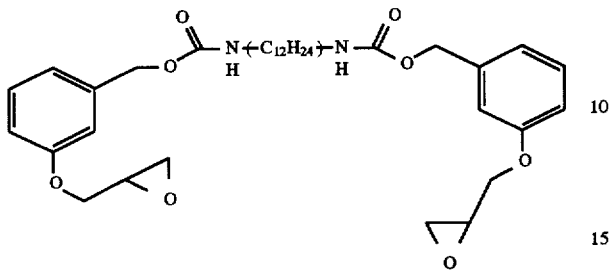

Into a 100 mL flask equipped with a thermometer, and magnetic stir bar, and sealed to the environment with rubber septa was weighed 1, 12-diisocyanatododecane (14.58 g, 0.0577 mole), 3-glycidyloxybenzyl alcohol (21.86 g, 0.121 mole) and 32.5 mL toluene. The cloudy mixture was stirred at 10°–20° C. in a cool water bath when dibutyl tin dilaurate was introduced by dipping the end of a 9 inch glass pipette into the tin catalyst and then mixing the end of the pipette into the reaction mixture. After mixing for 5 hours the mixture became a solid white mass. The solid was broken up with a spatula and 50 mL toluene was introduced to facilitate stirring. After a total of 7 hours reaction time, an IR trace indicated that essentially all isocyanate functionality had reacted. Toluene (80 mL) and methylene chloride (160 mL) were used to transfer the milky mixture to a single neck R B flask. Solvent was removed on a rotary evaporator to 80° C. Subsequent removal of solvent and unreacted alcohol was carried out on a Kugelrohr apparatus to 120° C./0.1 mmHg. The product was isolated as a white solid in 99% yield and characterized by IR and $^1$H-NMR spectroscopy. The epoxy equivalent weight was measured as WPE=319 (theoretical WPE=306.31).

Example V

In this example, glycidyloxybenzyl alcohols were reacted with various flexible diacids.

Preparation of the bis(3-glycidyloxybenzyl) ester of a mixture of undecanedioic acid, dodecanedioic acid, and sebacic acid (EPOXY G)

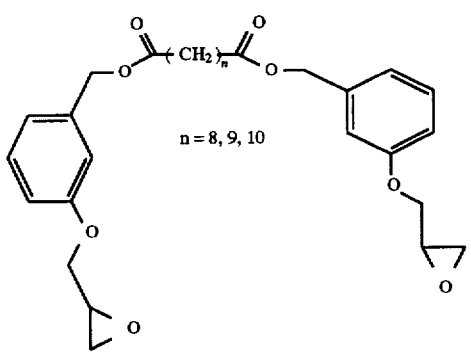

The mixture of undecanedioic acid, dodecanedioic acid, and sebacic acid is available under the tradename COR-FREE M1 from Aldrich Chemical Co. and is a DuPont product. The bis(3-glycidyloxybenzyl) ester was prepared as described above except that the CORFREE M1 was used in place of the dimer acid. The product was isolated in 98% yield and characterized by IR and $^1$H-NMR spectroscopy. The epoxy equivalent weight was measured as WPE=269.4 (theoretical WPE=265.5).

Preparation of the bis(3-glycidyloxybenzyl) ester of 3,6,9-trioxaundecanedioic acid (EPOXY H)

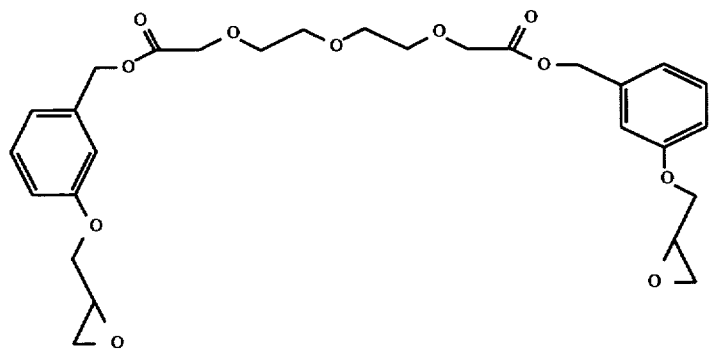

The 3,6,9-trioxaundecanedioic acid is an experimental material available from Hoechst Celanese and was used in place of the dimer acid. The trioxaundecanedioic acid (30 g) and 3-glycidyloxybenzyl alcohol (44.54 g) were mixed and treated with dicyclohexylcarbodiimide (50.88 g) and catalytic 4-dimethylaminopyridine (DMAP) (0.2998 g) in methylene chloride as described above. The product was isolated in 89% yield and characterized by IR and $^1$H-NMR spectroscopy. The epoxy equivalent weight was measured as WPE=285.1 (theoretical WPE=286.3).

Preparation of the (3-glycidyloxybenzyl) ester of octanoic acid (EPOXY I)

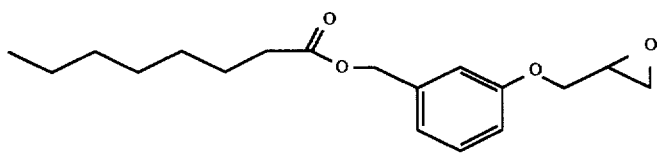

This product was prepared similarly to Epoxy G and H and is useful as a reactive diluent. Octanoic acid (30 g) and glycidyloxybenzyl alcohol (38.24 g) were treated under the dicyclohexylcarbodiimide (43.74 g) dehydrative conditions with catalytic DMAP (0.2572 g) in methylene chloride. The product was isolated as described above in 98% yield and characterized by IR and $^1$H-NMR spectroscopy. The epoxy equivalent weight was measured as WPE=306.2 (theoretical WPE=306.4).

Preparation of the (3-glycidyloxybenzyl) ester derived from poly(tetrahydrofuran) trimer (EPOXY J)

To a 250 mL flask with mechanical stirrer, thermometer, condenser, and $N_2$ purge was added poly(tetrahydrofuran) trimer (available from BASF, polyTHF-250; OH#=479.2; 25 g, 0.213 mole hydroxy functionality), succinic anhydride (21.5 g, 0.2156 mole), and toluene (20 mL). Heat was applied to maintain a mild reflux. After 3.5 hours of reaction time, the anhydride absorbance had disappeared from the IR trace. The mixture was cooled, and to this was added an additional 70 mL of toluene, 3-glycidyloxybenzyl alcohol (39.32 g), and DMAP (0.2648 g). This mixture was further cooled to 0°–5° C. at which point the addition of a DCC solution (44.80 g DCC dissolved in 50 mL toluene) was initiated. The addition was completed after 35 minutes, and the mixture was stirred for a further 4 hours. The IR trace showed no change in DCC or ester absorbance from the previous scan, and so the reaction was filtered to remove dicyclohexyl urea by-product. Amberlyst 15 ($H^+$ form, 14 mL) was added, stirred for 30 minutes, and filtered. Acetic acid (2 mL of a 50% aqueous solution) was added and stirred until the residual DCC peak was absent from the IR trace. Solid sodium bicarbonate and then sodium carbonate were added until a pH of 7 was achieved. The mixture was filtered, dried over $MgSO_4$, refiltered, and the solvent was removed on a rotary evaporator. Residual solvent and unreacted benzyl alcohol were further removed on a Kugelrohr apparatus to 122° C./0.1 mmHg. The product was isolated in 96% yield, and characterized by $^1$H-NMR, IR spectroscopy, and found to have an epoxy equivalent weight as WPE=394 (theoretical WPE=380).

Example VI

Comparative

This example gives the preparation of comparative samples of epoxy resins that do not contain the terminal phenyl groups.

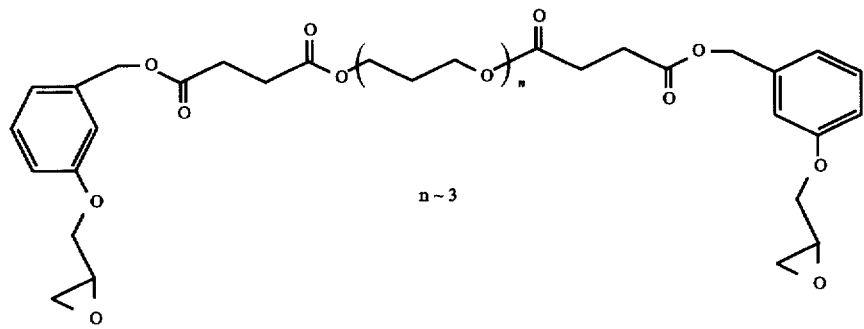

n ~ 3

Preparation of the bis O-(glycidyl)carbamate of dimer diisocyanate (EPOXY C)

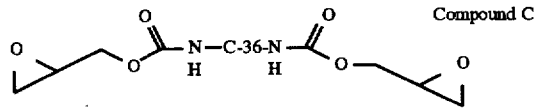

Compound C

Dimer diisocyanate (DDI-1410, 200 g, 0.6686 mol NCO) was weighed directly into a 500 mL multineck R B flask which was equipped with mechanical stirrer, thermometer, and $N_2$ purge. Then, glycidol (68 mL, 1.003 mol) was added along with 100 mL toluene. To this non-homogeneous mixture was added one drop of dibutyl tin dilaurate (DBTL) from a plastic disposable pipette. The mixture became completely clear and homogeneous 80 minutes after the addition of the DBTDL. An exotherm to 30° C. was observed while the flask was immersed in a cool water bath to which was added some dry ice to keep the temperature below 30° C. After 7.5 hours of reaction time (disappearance of NCO in the IR trace), the reaction mixture was passed over a silica column prepared in a 1 L slow add funnel by first slurrying ~250 mL of 30–60 mesh silica in EtOAc then layering on top of this ~150 mL of 70–230 mesh silica. The product was eluted with ~1.5 L EtOAc. The solvent was removed on the roto-vap, then on the Kugelrohr apparatus to 80° C./2.0 mmHg. The product was a pale yellow viscous oil (245.6 g, 99 8% yield) and was structurally confirmed by IR, $^1$H, and $^{13}$C-NMR spectroscopy. The epoxy content was measured as WPE=405 (theoretical WPE=368).

Preparation of dimer acid diglycidyl ester (EPOXY E)

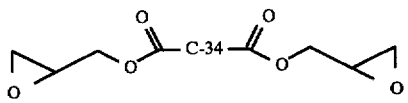

This material can be purchased commercially as EPON 871 from Shell Chemical Co. or prepared in a low chlorine contaminated version as described below. In either case the material behaves similarly with respect to cure rate and thermal stability.

Preparation of the diglycidyl ester of dimer acid (Empol 1024) with low chlorine: A multi-necked round bottom flask equipped with mechanical stirrer, thermometer, $N_2$ purge and slow-addition funnel was charged with 50.00 g (0.0868 moles) of Empol 1024 dimer acid, 19.29 g (0.2604 moles) glycidol, 200 ml of toluene and a catalytic amount (0.212 g, 0.0017 moles) of 4-dimethylaminopyridine. The reaction was cooled to 0°–5° C. and to this was added a solution of 36.48 g (0.1771 moles) 1,3-dicyclohexylcarbodiimide in 100 ml of toluene over a period of 1 hour. After the slow-add was complete the reaction was held at 0°–5° C. for 15 minutes. The reaction solution was then held at 10°–15° C. for two hours. The reaction was determined to be complete by IR (presence of ester at 1735 cm$^{-1}$) and the disappearance of the 1,3-dicyclohexylcarbodiimide (2120 cm$^{-1}$). The product solution was then cooled to 0°–5° C., held for 15 minutes then filtered to remove the 1,3-dicyclohexylurea byproduct. The product solution is then chilled to 10°–15° C. with stirring and to this was added a solution of 20 ml of 50:50 water:methanol and 34 ml of Amberlyst 15 (H$^+$ form). The reaction was then filtered and the solvent was removed using a rotory evaporator under reduced pressure. The product was then dissolved in 30 ml toluene and stored overnight in a freezer. The following day the solution was filtered cold, then the solvent was removed using a rotory evaporator under reduced pressure. Residual solvent and any remaining glycidol were subsequently removed using a kugelrohr apparatus (80° C./0.1–0.2 mmHg vacuum ). The product was isolated as an oil (46.48 g, 78% yield) and was characterized as follows: IR spectrum: ester at 1735 cm$^{-1}$. Epoxy equivalent weight: WPE=359 (theoretical=344).

Example VII

Chlorine Content of Samples

Several samples of epoxy resins were tested for total chlorine and hydrolyzable chlorine content according to the test methods described in this specification, and the results are tabulated here.

| EPOXY (ppm) | CHLORINE CONTENT OF EPOXY RESINS | | |
|---|---|---|---|
| | Total Chlorine (ppm) | Hydrolyzable Chlorine (ppm) | Bound Chlorine |
| A | 283 | 26 | 257 |
| B | 319 | 39 | 280 |
| 3-glycidyloxy-benzyl alcohol | 805 | 82 | 723 |
| C | 282 | 185 | 97 |
| D | 674 | 352 | 322 |

In the above table, the values for the 3-glycidyloxybenzyl alcohol and for EPOXY B from which it is derived indicate that the bulk of chlorine contamination comes from the starting alcohol. The chlorine content of EPOXY B is nearly identical to the calculated dilution factor accounting for the increased weight when the alcohol is converted to this ester. For example, 805 ppm×(360/906)=320 ppm. Therefore, any purification manipulation that can be carried out to reduce the chlorine content of the 3-glycidyloxybenzyl alcohol will result in lower chlorine contamination in the final flexible epoxide product.

Purification of 3-glycidyloxybenzyl alcohol: In another preparation of the 3-glycidyloxybenzyl alcohol as described above, the product was characterized by $^1$H-NMR and found to have a WPE=178 and total chlorine=317 ppm and hydrolyzable chlorine=120 ppm. This product (50 g) was added with methyl isobutyl ketone (50 mL) and 1N KOH (50 mL) to a 250 mL flask equipped with mechanical stirrer and thermometer. The mixture was stirred well and heated to 40°–45° C. for 4 hours. The flask was cooled and the contents transferred to a separatory funnel. The phases were separated and the organic layer was washed with 10% (3×100 mL) until the pH=7. The organic layer was dried over MgSO$_4$, filtered, and the solvent removed on a rotary evaporator. The purified product was distilled on a Kugelrohr apparatus at 110° C./0.25 mmHg. The purified material was found to have a WPE=177 and total chlorine=129 ppm and hydrolyzable chlorine=none detected. If this purified epoxy alcohol product was used to generate EPOXY B, then EPOXY B would have a total chlorine=51 ppm. Calculated as follows: 129 ppm×(360/906)=51 ppm.

Example VIII

Flexibility, Strength and Snap-Cure of Epoxies

The suitability of these epoxy resins for use in microelectronics applications was tested by measuring their flexibility and strength after they are formulated with silver flakes and used to bond silicon chips to a metal lead frame substrate.

Adhesive Formulations. The sample epoxies were formulated into a die attach adhesive comprising in parts by weight: 70 parts epoxy resin, 30 parts Bisphenol A diglycidyl ether (Bis-A) (sold under the tradename EPON 830, a product of Shell Corporation), 5 parts 2-ethyl-4-methyl imidazole (2E4MZ); this formulation was admixed with 80% by weight silver flakes until the silver was fully wetted out. The mixture was degassed under vacuum at room temperature for 15–20 minutes, and then allowed to sit at room temperature with frequent stirring for 60 minutes.

Measurements of flexibility and strength were taken on the cured epoxies. Flexibility was determined by measuring the radius of curvature, which was greater than 300 mm.

(The higher the radius of curvature, the less chip warpage, which in turn implies a flexible adhesive.) An indication of the flexibility was also provided by the glass transition temperatures (Tg), which were low for the cured epoxies. Strength was measured as die shear, which is the force required to remove a bended chip from the metal substrate; for these epoxies, the die shear was greater than or equal to 10 MPa when snap-cured and greater than or equal to 25 MPa when oven-cured. As determined by the time needed to 100% cure, these epoxies could be snap-cured.

Die Shear. Silicon chips (80×80 mil$^2$) were coated on one side with the adhesive formulation and placed on a copper lead frame (D/L) and cured in a 175° C. oven for one hour. The samples were tested after cure for die shear strength at room temperature (RT). Die shear strength was measured using a Hybrid Machine Products Corp. die shear tester (Model 1750)/Chatilion DFI 50 digital force gauge. The force required to remove the bonded die was read in kg units, and converted to a die shear strength in MPa averaged over ten samples. Preferred die shear values are those of 5 MPa or greater. Snap-cured samples were prepared similarly, except that the specimens were cured on a pre-warmed hot-plate at 180° C. for the time as prescribed in Table 1.

Radius of Curvature. Each epoxy to be tested was prepared, degassed, and aged for one hour as described above. Silicon chips (200×600 mil$^2$) were coated with adhesive on one side and placed on a lead frame and cured in a 175° C. oven for one hour. The radius of curvature for the cured samples was measured using a Tokyo Seimitsu SURFCOM surface texture measuring instrument and reported in millimeter (mm) units, averaged over three samples. Preferred radius of curvature values are those of 300 mm or greater.

Glass Transition Temperature. Glass Transition (Tg) temperatures were measured using a Perkin Elmer DSC. In the case of neat resins, the sample was preheated to 50° C. and then quench cooled to −70° C. It was then heated at a rate of 20° C. per minute until the Tg was reached. To measure the Tg of the cured resins, samples were formulated with 5 pph 2-ethyl-4-methyl imidazole and then heated to 200° C. to ensure full cure. After quench cooling to −40° C., the samples were heated at a rate of 20° C. per minute until the Tg was reached.

The die shear strength, time to snap-cure, radius of curvature and Tg for several of the samples are set out in the following Table 1.

TABLE 1

| EPOXY | DIE SHEAR (MPa) | | Time to Snap Cure | ROC (mm) | Tg °C. | |
|---|---|---|---|---|---|---|
| | Oven @ 175° | Snap @ 180° | | | Neat | Cured |
| A | chip failure | 38.3 | 1.0 min | 316 | −10.73 | 51.93 |
| B | 35.2 | 15.4 | 2.0 | 404 | −51.10 | −9/46 |
| C | 16.3 | 5.7 | 1.0 | 490 | −40.03 | −17.63 |
| D | 32.0 | 11.3 | 1.5 | 323 | −28.97 | 16.82 |
| E | 17.3 | 4.7 | 2.0 | 344 | −39.97 | −25.31 |
| G | 42.5 | 17.4 | 1.25 | 334 | | |
| G* | 28.6 | 11.8 | 1.75 | 498 | | |
| H | 32.3 | 13.6 | 1.5 | 428 | | |

*neat - not as blend w/bis A epoxy

Example IX

Thermal Properties

DSC Analysis. Several of the sample epoxy resins formulated into adhesives were tested for their ability to be snap-cured by DSC analysis using a Perkin-Elmer Differential Scanning Calorimeter. DSC measures the onset and end of exotherm, which is commensurate with cure. The formulations, as described in Example VIII, were cured in the DSC pan on a hot plate at 180° C. for a prescribed time, a DSC trace was then run to determine the extent of reaction, which is extrapolated from the residual exotherm:

$$\frac{\Delta H_{initial} - \Delta H_{remaining}}{\Delta H_{initial}} \times 100\% = \% \text{ cure}$$

Curing times that occur in a span of 50° C. or less indicate that those formulations can be snap-cured. The onset and end of exotherm for the samples is given in Table 2 and show that several of the epoxies, when used in an imidazole-catalyzed formulation have the capability of being snap-cured.

Data from the DSC curves were plotted as percent cure versus time in FIG. 1, and again show that the curing rate for the inventive compounds meet the requirement for snap-cure. As will be understood, the steeper the slope of the curves, the faster the cure. For the tested samples, the order of curing was C~A>D>B>E.

TABLE 2

| EPOXY | ONSET OF EXO | END OF EXO | PEAK OF EXO | ΔH kJ/mol |
|---|---|---|---|---|
| E | 79° C. | 198° C. | 130.0° C. | 139.9 |
| A | 100.0 | 148.5 | 131.0 | 83.6 |
| B | 97.0 | 199.0 | 146.7 | 76.2 |
| C | 92.4 | 148.4 | 124.2 | 87.2 |
| D | 100.7 | 148.4 | 129.7 | 84.6 |
| G | 108.7 | 157.8 | 141.0 | 82.0 |
| H | 125.4 | 169.8 | 147.2 | 64.9 |

Figure 3:
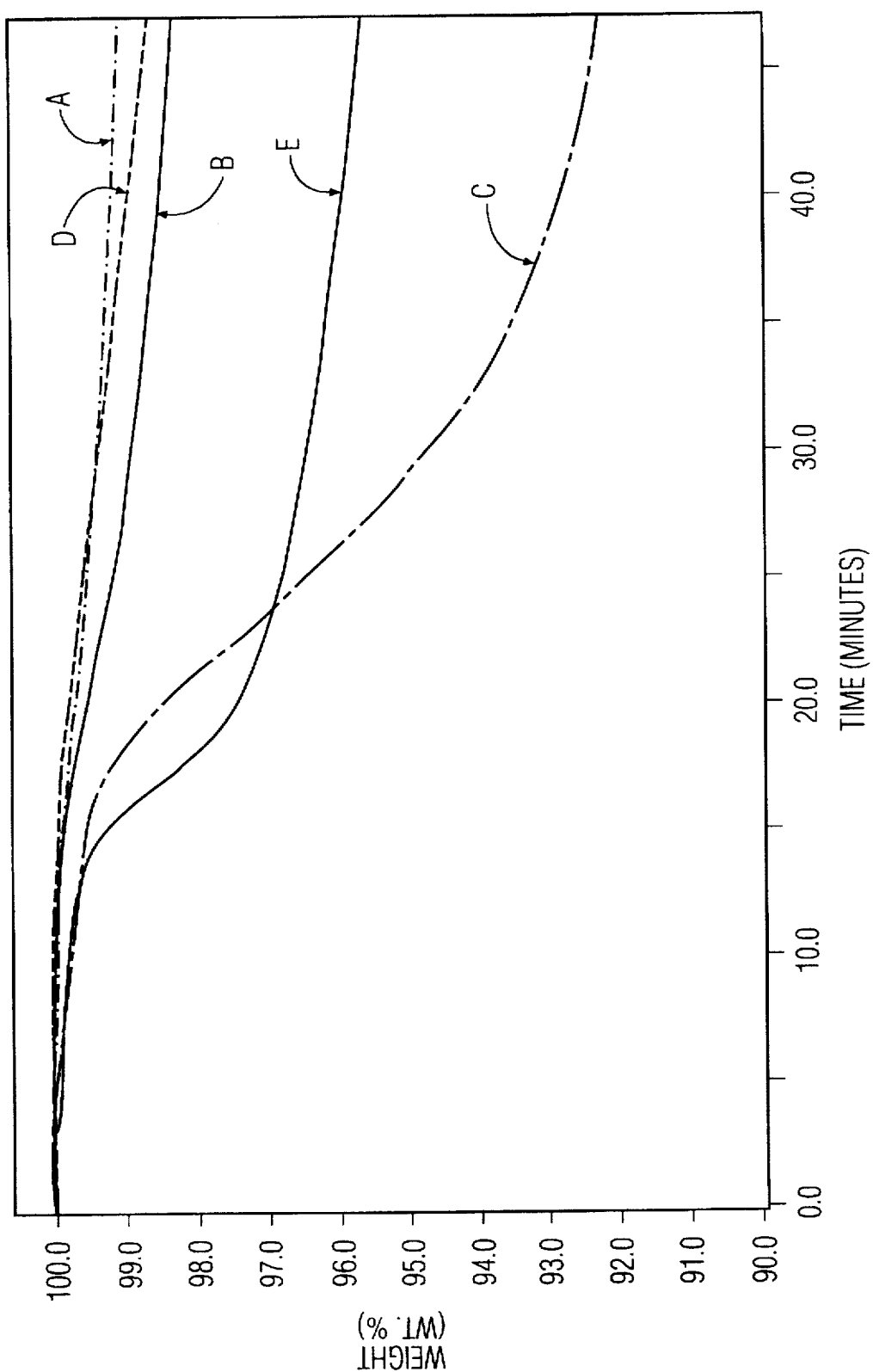
FIG. 3 is a graph of the thermogravimetric analysis of inventive sample epoxy resins and shows their thermal stability when heated from 30°–200° C. at 10° C. per minute and held at 200° C. for 30 minutes.
Figure 4:
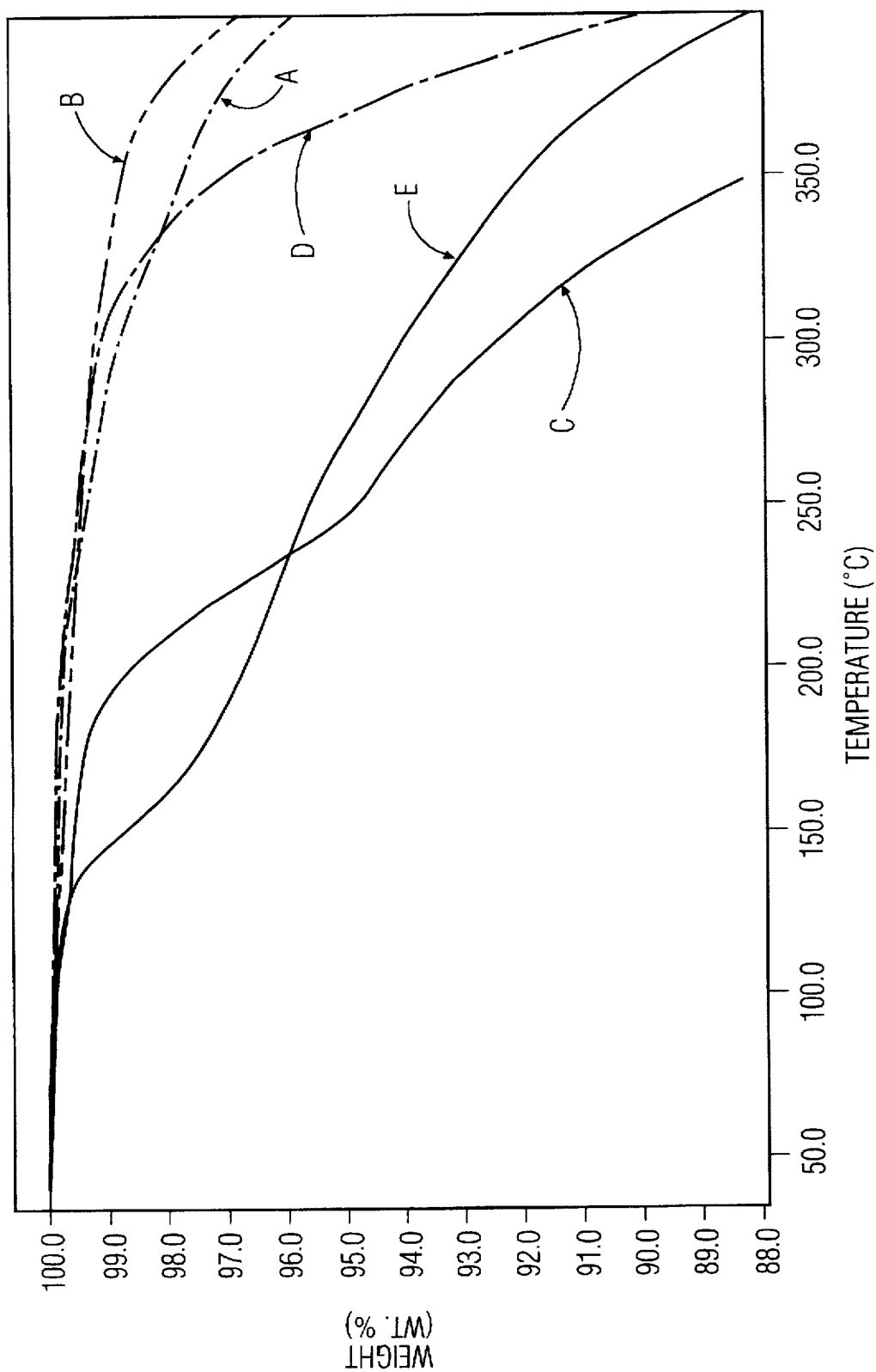
FIG. 4 is a graph of the thermogravimetric analysis of the inventive sample epoxy resins in the presence of curing catalyst (2-ethyl-4-methyl imidazole) heated from 30°–350° C. at 10° C. per minute.. This graph shows weight loss during the cure process and demonstrates that comparative epoxies C and E lose substantial weight in the 200°–250° C. range, which is the temperature range for wire bonding and solder reflow in the manufacture of electronics devices.

TGA Analysis. Thermogravimetric analysis (TGA) was performed on several of the samples using a Perkin Elmer TGA unit. TGA is a measure of the loss of weight when a sample is subjected to a heating cycle. The formulations described in Example VIII were subjected to analysis under a heating ramp of 30° to 200° C. at an increase in temperature of 10° per minute, and a 30 minute hold at 200° C. for a total of 50 minutes. The results are given in Table 3. FIGS. 3 and 4 show that the samples exhibit far superior thermal stability either as neat materials or even more notably in the presence of an imidazole curing catalyst.

TABLE 3

| EPOXY | TGA % wt loss to 175° C. 10°/min | TGA % wt loss to 200° C. 10°/min | TGA % wt loss @ 200° C. 30 min hold | TGA % wt loss to 200° C. with 2E4MZ |
|---|---|---|---|---|
| E | 0.548 | 1.41 | 4.25 | 3.356 |
| A | 0.108 | 0.299 | 0.93 | 0.303 |
| B | 0.269 | 0.547 | 1.70 | 0.377 |
| C | 0.588 | 0.682 | 7.70 | 1.398 |
| D | 0.034 | 0.196 | 1.34 | 0.314 |

We claim:

1. A flexible epoxy compound having the structural formula

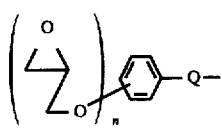

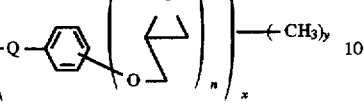

in which Q is

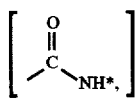

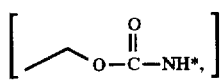

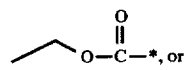

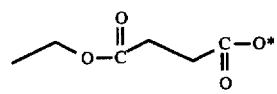

where * indicates the point of attach to the flexible chain; the flexible chain is a $C_6$–$C_{50}$ alkylene or alkyleneoxy group when x is 0, y is 1, and n is 1; and the flexible chain is a $C_{10}$–$C_{50}$ alkylene or alkyleneoxy group when x is 1, y is 0, and n is 1–3.

2. A flexible compound according to claim 1 having the structural formula:

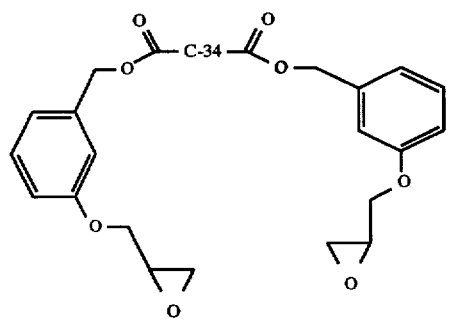

in which C-34 is the residual hydrocarbon chain of dimer acid.

3. A flexible compound according to claim 1 having the structural formula:

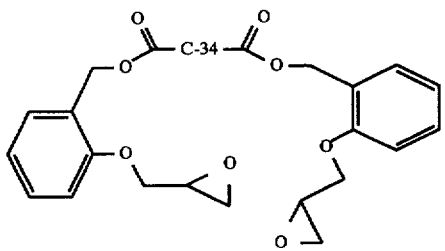

in which C-34 is the residual hydrocarbon chain of dimer acid.

4. A flexible compound according to claim 1 having the structural formula:

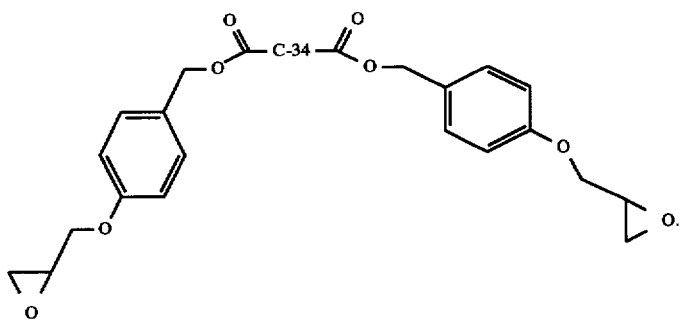

in which C-34 is the residual hydrocarbon chain of dimer acid.

5. A flexible epoxy compound according to claim 1 having the structural formula:

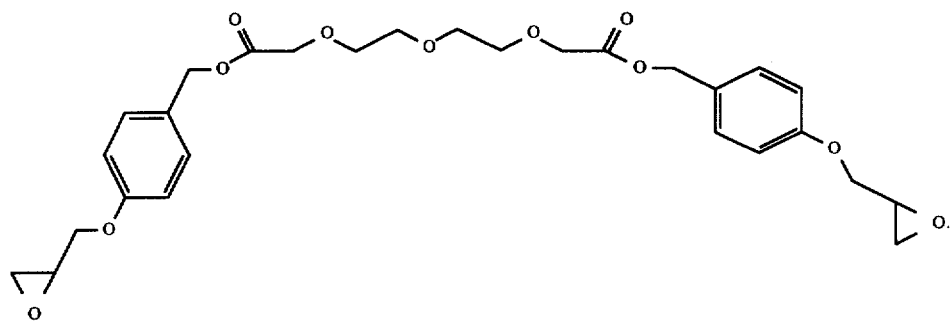
6. A flexible epoxy compound according to claim 1 having the structural formula:
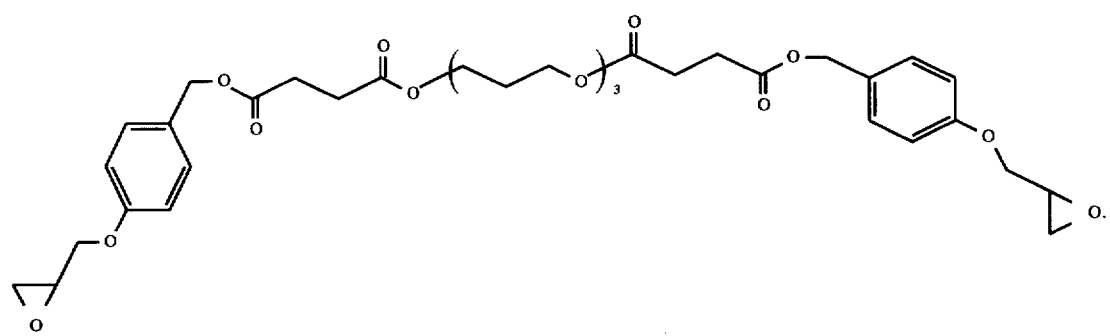
7. A flexible epoxy compound according to claim 1 having the structure:
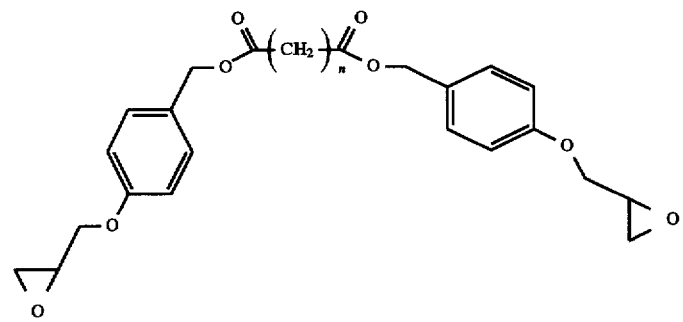
in which n=8, 9, or 10.
8. A flexible epoxy compound according to claim 1 having the structural formula:
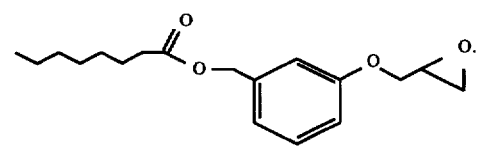
9. An adhesive for use in microelectronics applications containing a flexible epoxy according to claim 1.
* * * * *